(12) United States Patent
Silverman et al.

(10) Patent No.: US 12,357,446 B2
(45) Date of Patent: Jul. 15, 2025

(54) MATCHED STENT COVER

(71) Applicant: W. L. Gore & Associates, Inc., Newark, DE (US)

(72) Inventors: James D. Silverman, Flagstaff, AZ (US); Craig W. Irwin, Parks, AZ (US); Tyson J. Skelton, Flagstaff, AZ (US)

(73) Assignee: W. L. Gore & Associates, Inc., Newark, DE (US)

( * ) Notice: Subject to any disclaimer, the term of this patent is extended or adjusted under 35 U.S.C. 154(b) by 27 days.

(21) Appl. No.: 16/754,968

(22) PCT Filed: Oct. 9, 2018

(86) PCT No.: PCT/US2018/054915
§ 371 (c)(1),
(2) Date: Apr. 9, 2020

(87) PCT Pub. No.: WO2019/074869
PCT Pub. Date: Apr. 18, 2019

(65) Prior Publication Data
US 2020/0237497 A1   Jul. 30, 2020

Related U.S. Application Data

(60) Provisional application No. 62/569,805, filed on Oct. 9, 2017.

(51) Int. Cl.
*A61F 2/07* (2013.01)

(52) U.S. Cl.
CPC ........ *A61F 2/07* (2013.01); *A61F 2230/0091* (2013.01); *A61F 2250/0028* (2013.01)

(58) Field of Classification Search
CPC ................ A61F 2/07; A61F 2230/0091; A61F 2250/0028; A61F 2/06; A61F 2/90; A61F 2002/0072–0077; D03D 3/02; B29K 2027/18; C08L 27/18
See application file for complete search history.

(56) References Cited

U.S. PATENT DOCUMENTS

| | | | |
|---|---|---|---|
| 3,953,566 A | 4/1976 | Gore | |
| 4,187,390 A | 2/1980 | Gore | |
| 4,332,035 A | 6/1982 | Mano | |
| 4,877,661 A | 10/1989 | House et al. | |

(Continued)

FOREIGN PATENT DOCUMENTS

| | | |
|---|---|---|
| CA | 2462509 A1 | 4/2003 |
| CN | 101420913 A | 4/2009 |

(Continued)

OTHER PUBLICATIONS

International Search Report and Written Opinion received for PCT Patent Application No. PCT/US2018/054915, mailed on Apr. 2, 2019, 18 pages.

(Continued)

*Primary Examiner* — Melanie R Tyson
*Assistant Examiner* — Rebecca Lynee Zimmerman

(57) ABSTRACT

Various aspects of the present disclosure are directed toward implantable medical devices that include a frame and a tubular member attached to the frame. The tubular member includes one or more fibrils or a strength in alignment with one or more struts of the frame.

10 Claims, 7 Drawing Sheets

(56) References Cited

U.S. PATENT DOCUMENTS

| | | | |
|---|---|---|---|
| 4,955,899 A | 9/1990 | Della et al. |
| 5,026,513 A | 6/1991 | House et al. |
| 5,064,435 A | 11/1991 | Porter |
| 5,071,609 A | 12/1991 | Tu et al. |
| 5,476,589 A | 12/1995 | Bacino |
| 5,534,007 A | 7/1996 | St et al. |
| 5,549,663 A | 8/1996 | Cottone, Jr. |
| 5,673,102 A | 9/1997 | Suzuki et al. |
| 5,708,044 A | 1/1998 | Branca |
| 5,718,973 A | 2/1998 | Lewis et al. |
| 5,720,776 A | 2/1998 | Chuter et al. |
| 5,749,852 A | 5/1998 | Schwab et al. |
| 5,752,934 A | 5/1998 | Campbell et al. |
| 5,759,192 A | 6/1998 | Saunders |
| 5,769,884 A | 6/1998 | Solovay |
| 5,772,884 A | 6/1998 | Tanaka et al. |
| 5,788,626 A | 8/1998 | Thompson |
| 5,814,405 A | 9/1998 | Branca et al. |
| 5,824,043 A | 10/1998 | Cottone, Jr. |
| 5,843,158 A | 12/1998 | Lenker et al. |
| 5,843,161 A | 12/1998 | Solovay |
| 5,843,171 A | 12/1998 | Campbell et al. |
| 5,853,419 A | 12/1998 | Imran |
| 5,925,061 A | 7/1999 | Ogi et al. |
| 5,935,162 A | 8/1999 | Dang |
| 5,957,974 A | 9/1999 | Thompson et al. |
| 6,010,529 A | 1/2000 | Herweck et al. |
| 6,013,854 A | 1/2000 | Moriuchi |
| 6,042,588 A | 3/2000 | Munsinger et al. |
| 6,042,605 A | 3/2000 | Martin et al. |
| 6,042,606 A | 3/2000 | Frantzen |
| 6,110,198 A | 8/2000 | Fogarty et al. |
| 6,156,064 A | 12/2000 | Chouinard |
| 6,161,399 A | 12/2000 | Jayaraman |
| 6,165,211 A | 12/2000 | Thompson |
| 6,174,329 B1 | 1/2001 | Callol et al. |
| 6,190,406 B1 | 2/2001 | Duerig et al. |
| 6,217,609 B1 | 4/2001 | Haverkost |
| 6,245,012 B1 | 6/2001 | Kleshinski |
| 6,261,320 B1 | 7/2001 | Tam et al. |
| 6,261,620 B1 | 7/2001 | Leadbeater |
| 6,315,791 B1 | 11/2001 | Gingras et al. |
| 6,336,937 B1 | 1/2002 | Vonesh et al. |
| 6,352,552 B1 | 3/2002 | Levinson et al. |
| 6,379,382 B1 | 4/2002 | Yang |
| 6,423,091 B1 | 7/2002 | Hojeibane |
| 6,436,132 B1 | 8/2002 | Patel et al. |
| 6,461,665 B1 | 10/2002 | Scholander |
| 6,488,701 B1 | 12/2002 | Nolting et al. |
| 6,541,589 B1 | 4/2003 | Baillie |
| 6,620,190 B1 | 9/2003 | Colone |
| 6,626,939 B1 | 9/2003 | Burnside et al. |
| 6,673,102 B1 | 1/2004 | Vonesh et al. |
| 6,673,107 B1 | 1/2004 | Brandt et al. |
| 6,716,239 B2 * | 4/2004 | Sowinski ............... B29C 55/22 |
| | | 623/1.53 |
| 6,730,120 B2 | 5/2004 | Berg et al. |
| 6,755,856 B2 | 6/2004 | Fierens et al. |
| 6,758,858 B2 | 7/2004 | Mccrea et al. |
| 6,890,350 B1 | 5/2005 | Walak |
| 7,022,132 B2 | 4/2006 | Kocur |
| 7,049,380 B1 | 5/2006 | Chang et al. |
| 7,083,642 B2 | 8/2006 | Sirhan et al. |
| 7,105,018 B1 | 9/2006 | Yip et al. |
| 7,306,729 B2 | 12/2007 | Bacino et al. |
| 7,419,678 B2 | 9/2008 | Falotico |
| 7,462,675 B2 | 12/2008 | Chang et al. |
| 7,531,611 B2 | 5/2009 | Sabol et al. |
| 7,704,274 B2 | 4/2010 | Boyle et al. |
| 7,789,908 B2 | 9/2010 | Sowinski et al. |
| 7,811,314 B2 | 10/2010 | Fierens et al. |
| 7,815,763 B2 | 10/2010 | Fierens et al. |
| 7,887,562 B2 | 2/2011 | Young et al. |
| 7,927,364 B2 | 4/2011 | Fierens et al. |
| 7,927,365 B2 | 4/2011 | Fierens et al. |
| 7,935,141 B2 | 5/2011 | Randall et al. |
| 7,967,829 B2 | 6/2011 | Gunderson et al. |
| 8,048,440 B2 | 11/2011 | Chang et al. |
| 8,545,525 B2 | 10/2013 | Surti et al. |
| 8,585,753 B2 | 11/2013 | Scanlon et al. |
| 8,728,103 B2 | 5/2014 | Surti et al. |
| 8,801,774 B2 | 8/2014 | Silverman |
| 8,936,634 B2 | 1/2015 | Irwin et al. |
| 9,241,695 B2 | 1/2016 | Peavey et al. |
| 9,345,601 B2 | 5/2016 | Jantzen et al. |
| 9,399,085 B2 | 7/2016 | Cleek et al. |
| 9,554,786 B2 | 1/2017 | Carley et al. |
| 9,681,948 B2 | 6/2017 | Levi et al. |
| 9,737,422 B2 | 8/2017 | Armstrong et al. |
| 9,795,496 B2 | 10/2017 | Armstrong et al. |
| 9,833,343 B2 | 12/2017 | Burnside et al. |
| 9,839,540 B2 | 12/2017 | Armstrong et al. |
| 9,931,193 B2 | 4/2018 | Cully et al. |
| 10,166,128 B2 | 1/2019 | Armstrong et al. |
| 10,279,084 B2 | 5/2019 | Goepfrich et al. |
| 10,335,298 B2 | 7/2019 | Armstrong et al. |
| 10,507,124 B2 | 12/2019 | Armstrong et al. |
| 2001/0032009 A1 * | 10/2001 | Layne ...................... A61F 2/07 |
| | | 623/1.13 |
| 2001/0053929 A1 | 12/2001 | Vonesh et al. |
| 2002/0038140 A1 | 3/2002 | Yang et al. |
| 2002/0076542 A1 | 6/2002 | Kramer et al. |
| 2002/0161388 A1 | 10/2002 | Samuels et al. |
| 2002/0198588 A1 | 12/2002 | Armstrong et al. |
| 2003/0055494 A1 | 3/2003 | Bezuidenhout et al. |
| 2003/0060871 A1 | 3/2003 | Hill et al. |
| 2003/0180488 A1 | 9/2003 | Lim et al. |
| 2004/0024442 A1 | 2/2004 | Sowinski et al. |
| 2004/0024448 A1 | 2/2004 | Chang et al. |
| 2004/0044400 A1 | 3/2004 | Cheng et al. |
| 2004/0044401 A1 | 3/2004 | Bales et al. |
| 2004/0093065 A1 | 5/2004 | Yachia et al. |
| 2004/0098095 A1 * | 5/2004 | Burnside .................. A61F 2/07 |
| | | 623/1.13 |
| 2004/0133266 A1 | 7/2004 | Clerc et al. |
| 2004/0162606 A1 * | 8/2004 | Thompson ............... A61F 2/90 |
| | | 623/1.22 |
| 2004/0170782 A1 | 9/2004 | Wang et al. |
| 2004/0224442 A1 | 11/2004 | Grigg |
| 2004/0260277 A1 | 12/2004 | Maguire |
| 2005/0080476 A1 | 4/2005 | Gunderson et al. |
| 2005/0137680 A1 | 6/2005 | Ortiz et al. |
| 2005/0273149 A1 | 12/2005 | Tran et al. |
| 2005/0283224 A1 | 12/2005 | King |
| 2006/0009835 A1 | 1/2006 | Osborne et al. |
| 2006/0015171 A1 | 1/2006 | Armstrong |
| 2006/0036311 A1 | 2/2006 | Nakayama et al. |
| 2006/0106337 A1 | 5/2006 | Blankenship |
| 2006/0118236 A1 | 6/2006 | House et al. |
| 2006/0135985 A1 | 6/2006 | Cox et al. |
| 2006/0161241 A1 | 7/2006 | Barbut et al. |
| 2006/0190070 A1 | 8/2006 | Dieck et al. |
| 2006/0259133 A1 | 11/2006 | Sowinski et al. |
| 2006/0271091 A1 | 11/2006 | Campbell et al. |
| 2006/0276883 A1 | 12/2006 | Greenberg et al. |
| 2007/0012624 A1 | 1/2007 | Bacino et al. |
| 2007/0060999 A1 | 3/2007 | Randall et al. |
| 2007/0088421 A1 | 4/2007 | Loewen |
| 2007/0129786 A1 | 6/2007 | Beach et al. |
| 2007/0207186 A1 | 9/2007 | Scanlon et al. |
| 2007/0207816 A1 | 9/2007 | Spain, Jr. |
| 2007/0208421 A1 | 9/2007 | Quigley |
| 2007/0213800 A1 | 9/2007 | Fierens et al. |
| 2007/0250146 A1 | 10/2007 | Cully et al. |
| 2007/0250153 A1 | 10/2007 | Cully et al. |
| 2007/0254012 A1 | 11/2007 | Ludwig et al. |
| 2008/0051876 A1 | 2/2008 | Ta et al. |
| 2008/0097301 A1 | 4/2008 | Alpini et al. |
| 2008/0097401 A1 | 4/2008 | Trapp et al. |
| 2008/0097579 A1 | 4/2008 | Shanley et al. |
| 2008/0097582 A1 | 4/2008 | Shanley et al. |
| 2008/0119943 A1 | 5/2008 | Armstrong et al. |
| 2008/0319531 A1 | 12/2008 | Doran et al. |
| 2009/0005854 A1 | 1/2009 | Huang et al. |

(56) References Cited

U.S. PATENT DOCUMENTS

| | | |
|---|---|---|
| 2009/0030499 A1 | 1/2009 | Bebb et al. |
| 2009/0036976 A1 | 2/2009 | Beach et al. |
| 2009/0043373 A1 | 2/2009 | Arnault et al. |
| 2009/0104247 A1 | 4/2009 | Pacetti |
| 2009/0182413 A1 | 7/2009 | Burkart et al. |
| 2009/0306762 A1 | 12/2009 | Mccullagh et al. |
| 2009/0306766 A1 | 12/2009 | Mcdermott et al. |
| 2010/0016940 A1 | 1/2010 | Shokoohi et al. |
| 2010/0094394 A1 | 4/2010 | Beach et al. |
| 2010/0094405 A1 | 4/2010 | Cottone |
| 2010/0106240 A1 | 4/2010 | Duggal et al. |
| 2010/0159171 A1 | 6/2010 | Clough |
| 2010/0211166 A1 | 8/2010 | Miller et al. |
| 2010/0241214 A1 | 9/2010 | Holzer et al. |
| 2010/0256738 A1 | 10/2010 | Berglund |
| 2010/0286760 A1 | 11/2010 | Beach et al. |
| 2010/0305682 A1 | 12/2010 | Furst |
| 2011/0009953 A1 | 1/2011 | Luk et al. |
| 2011/0087318 A1 | 4/2011 | Daugherty et al. |
| 2012/0323211 A1 | 12/2012 | Ogle et al. |
| 2013/0131780 A1 | 5/2013 | Armstrong et al. |
| 2013/0183515 A1 | 7/2013 | White |
| 2013/0184807 A1 | 7/2013 | Kovach et al. |
| 2013/0197624 A1 | 8/2013 | Armstrong et al. |
| 2013/0204347 A1 | 8/2013 | Armstrong et al. |
| 2013/0245745 A1 | 9/2013 | Vong et al. |
| 2013/0253466 A1 | 9/2013 | Campbell et al. |
| 2013/0297003 A1 | 11/2013 | Pinchuk |
| 2014/0121746 A1 | 5/2014 | Kusleika et al. |
| 2014/0135897 A1 | 5/2014 | Cully et al. |
| 2014/0172066 A1 | 6/2014 | Goepfrich et al. |
| 2014/0180402 A1 | 6/2014 | Bruchman et al. |
| 2015/0005870 A1 | 1/2015 | Kovach et al. |
| 2015/0157770 A1 | 6/2015 | Cully et al. |
| 2015/0313871 A1 | 11/2015 | Li et al. |
| 2016/0015422 A1 | 1/2016 | De et al. |
| 2016/0184079 A1 | 6/2016 | Scutti et al. |
| 2017/0065400 A1 | 3/2017 | Armstrong et al. |
| 2017/0105854 A1 | 4/2017 | Treacy et al. |
| 2017/0106176 A1 | 4/2017 | Taft et al. |
| 2017/0216062 A1 | 8/2017 | Armstrong et al. |
| 2018/0177583 A1 | 6/2018 | Cully et al. |
| 2019/0125517 A1 | 5/2019 | Cully et al. |
| 2019/0209739 A1 | 7/2019 | Goepfrich et al. |
| 2019/0216592 A1 | 7/2019 | Cully et al. |
| 2020/0022828 A1 | 1/2020 | Armstrong et al. |
| 2020/0179663 A1 | 6/2020 | Mcdaniel et al. |
| 2021/0038413 A1 | 2/2021 | Cully et al. |
| 2021/0068996 A1 | 3/2021 | Armstrong et al. |
| 2021/0077246 A1 | 3/2021 | Cully et al. |
| 2021/0138121 A1 | 5/2021 | Cully et al. |
| 2021/0236139 A1 | 8/2021 | Connor |

FOREIGN PATENT DOCUMENTS

| | | |
|---|---|---|
| CN | 101926699 A | 12/2010 |
| CN | 201744060 U | 2/2011 |
| CN | 102015009 A | 4/2011 |
| CN | 103945796 A | 7/2014 |
| CN | 105025848 A | 11/2015 |
| EP | 0293090 A2 | 11/1988 |
| EP | 0313263 A2 | 4/1989 |
| EP | 0582870 A2 | 2/1994 |
| EP | 0775472 A2 | 5/1997 |
| EP | 0815806 A2 | 1/1998 |
| EP | 0893108 A2 | 1/1999 |
| EP | 1666003 A1 | 6/2006 |
| EP | 1946721 A1 | 7/2008 |
| EP | 2255750 A2 | 12/2010 |
| JP | 02-000645 A | 1/1990 |
| JP | 09-241412 A | 9/1997 |
| JP | 11-197252 A | 7/1999 |
| JP | 11-290448 A | 10/1999 |
| JP | 11-512635 A | 11/1999 |
| JP | 2001-509702 A | 7/2001 |
| JP | 2007-526098 A | 9/2007 |
| JP | 2008-506459 A | 3/2008 |
| JP | 2008-173461 A | 7/2008 |
| JP | 2010-500107 A | 1/2010 |
| JP | 2010-504174 A | 2/2010 |
| JP | 2010-535075 A | 11/2010 |
| JP | 2015-513931 A | 5/2015 |
| JP | 2018-134425 A | 8/2018 |
| JP | 2019-048083 A | 3/2019 |
| JP | 2021-122433 A | 8/2021 |
| RU | 2124986 C1 | 1/1999 |
| WO | 94/13224 A1 | 6/1994 |
| WO | 94/16802 A1 | 8/1994 |
| WO | 95/05555 A1 | 2/1995 |
| WO | 95/09586 A1 | 4/1995 |
| WO | 96/07370 A1 | 3/1996 |
| WO | 96/40348 A1 | 12/1996 |
| WO | 97/10871 A1 | 3/1997 |
| WO | 99/26558 A1 | 6/1999 |
| WO | 00/41649 A1 | 7/2000 |
| WO | 00/47271 A1 | 8/2000 |
| WO | 01/64278 A1 | 9/2001 |
| WO | 01/74272 A2 | 10/2001 |
| WO | 02/60506 A1 | 8/2002 |
| WO | 03/03946 A1 | 1/2003 |
| WO | 03/20175 A1 | 3/2003 |
| WO | 2004/000375 A1 | 12/2003 |
| WO | 2006/019626 A2 | 2/2006 |
| WO | 2006/058322 A2 | 6/2006 |
| WO | 2008/021002 A1 | 2/2008 |
| WO | 2008/028964 A2 | 3/2008 |
| WO | 2008/036870 A2 | 3/2008 |
| WO | 2008/049045 A2 | 4/2008 |
| WO | 2008/021006 A3 | 8/2008 |
| WO | 2008/097589 A1 | 8/2008 |
| WO | 2009/017827 A1 | 2/2009 |
| WO | 2009/100210 A1 | 8/2009 |
| WO | 2009/108355 A1 | 9/2009 |
| WO | 2010/006783 A1 | 1/2010 |
| WO | 2010/008570 A1 | 1/2010 |
| WO | 2010/030766 A1 | 3/2010 |
| WO | 2010/132707 A1 | 11/2010 |
| WO | 2010/150208 A2 | 12/2010 |
| WO | 2011/098565 A1 | 8/2011 |
| WO | 2011/132634 A1 | 10/2011 |
| WO | 2012/011261 A1 | 1/2012 |
| WO | 2012/099979 A1 | 7/2012 |
| WO | 2012/158944 A1 | 11/2012 |
| WO | 2013/074663 A2 | 5/2013 |
| WO | 2013/074990 A1 | 5/2013 |
| WO | 2013/109337 A1 | 7/2013 |
| WO | 2013/138789 A1 | 9/2013 |
| WO | 2017/038145 A1 | 3/2017 |
| WO | 2019/074869 A1 | 4/2019 |

OTHER PUBLICATIONS

Nakayama, Yasuhide. Microporous Stent Achieves Brain Aneurysm Occlusion Without Disturbing Branching Flow. NeuroNews Nov. 2012; 8:1-2.

Nishi S, Nakayama Y, Ishibashi-Ueda H, Okamoto Y, Yoshida M. Development of microporous self-expanding stent grafts for treating cerebral aneurysms: designing micropores to control intimal hyperplasia. J Artif Organs 2011; 14:348-356.

International Preliminary Report on Patentability received for PCT Patent Application No. PCT/US2018/054915, mailed on Apr. 23, 2020, 14 pages.

* cited by examiner

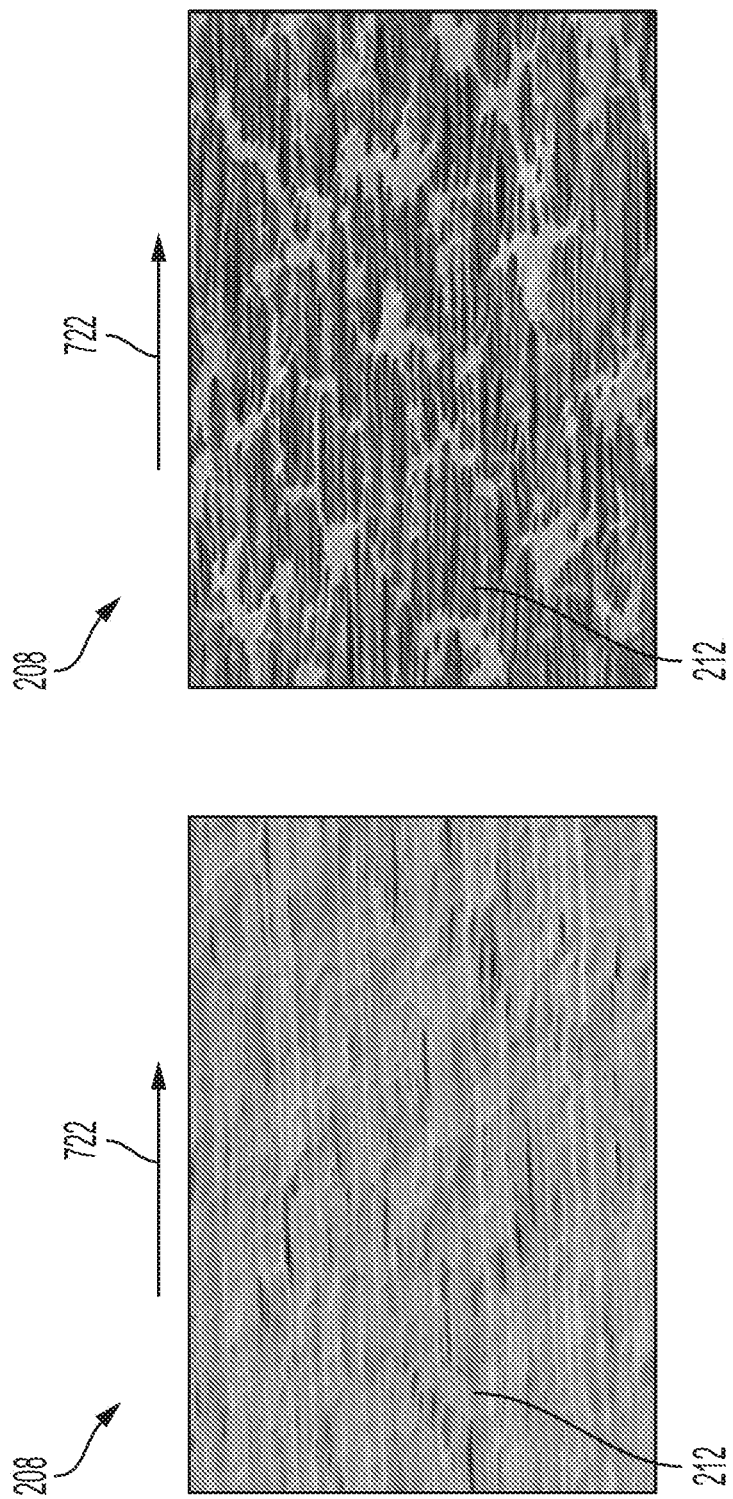

MATCHED STENT COVER

CROSS-REFERENCE TO RELATED APPLICATIONS

This application national phase application of PCT Application No. PCT/US2018/054915, internationally filed on Oct. 9, 2018, which claims the benefit of U.S. Provisional Application No. 62/569,805, filed Oct. 9, 2017, the entire contents of which are incorporated herein by reference for all purposes.

BACKGROUND

Medical stents are generally known. Stents, in combination with coverings, also can be used for the endovascular repair of aneurysms, an abnormal widening or ballooning of a portion of a body lumen which can be related to weakness in the wall of the body lumen. Various stent designs are known in the art. Stents typically are tubular, and are expandable or self-expand from a relatively small diameter to a larger diameter.

Braided stents are popular for bare metal constructs. Covering a braided stent has challenges in that the covering will wrinkle, stretch, or tear if it does not move in tandem with the wires.

SUMMARY

According to one example, ("Example 1"), an implantable medical device includes a frame having a plurality of struts overlapping and extending between a proximal end and a distal end of the frame; and a tubular member attached to the frame and including fibrils extending along the plurality of struts and configured to maintain alignment with the plurality of struts.

According to another example, ("Example 2") further to Example 1, the fibrils of the tubular member are axially aligned with the plurality of struts.

According to another example, ("Example 3") further to Examples 1 or 2, the fibrils extend in parallel with the plurality of struts.

According to another example, ("Example 4") further to Examples 1-3, the plurality of struts are braided and extend helically between the proximal end and the distal end of the frame, and the fibrils are configured to coincide with a geometry of the plurality of struts.

According to another example, ("Example 5") further to Example 4, the geometry of the plurality of struts changes in response to at least one of a length change of the frame and a circumferential change of the frame, and the fibrils are configured to orient with the plurality of struts in a direction extending toward the proximal end of the frame and a direction extending toward the distal end of the frame.

According to another example, ("Example 6") further to Examples 1-5, the plurality of struts include a first set of struts that extend at a first pitch toward the proximal end and a second set of struts that extend at a second pitch toward the distal end, and the fibrils include a first set of fibrils that extend at approximately the first pitch toward the proximal end and a second set of fibrils that extend at approximately the second pitch toward the distal end.

According to another example, ("Example 7") further to Example 6, the first set of fibrils overlap with the second set of fibrils throughout the tubular member.

According to another example, ("Example 8") further to Example 7, the fibrils are configured to shear relative to one another to maintain alignment with the plurality of struts in response to at least one of a length change of the frame and a circumferential change of the frame.

According to another example, ("Example 9") further to Examples 1-8, the tubular membrane is configured to allow expansion and contraction of the frame in response to at least one of a length change of the frame, a circumferential change of the frame, and angular displacement of the frame.

According to another example, ("Example 10") further to Example 9, the tubular member is configured to resist residual elastic strain acting against frame deformation in response to at least one of the length change of the frame, the circumferential change of the frame, and the angular displacement of the frame.

According to another example, ("Example 11"), an implantable medical device includes a frame having a plurality of struts overlapping and helically extending between a proximal end and a distal end of the frame; and a tubular member attached to the frame and including a primary strength oriented with the plurality of struts, the tubular member configured to maintain orientation of the primary strength with the plurality of struts in response to a force applied to the frame.

According to another example, ("Example 12") further to Example 11, the tubular member includes a first set of fibrils aligned with the plurality of struts to form the primary strength of the tubular member and a second set of fibrils unaligned with the plurality of struts.

According to another example, ("Example 13") further to Example 12, the tubular member includes a greater number of the first set of fibrils than a number of the second set of fibrils.

According to another example, ("Example 14") further to Examples 12-13, lengths of the first set of fibrils are greater than lengths of the second set of fibrils.

According to another example, ("Example 15") further to Examples 12-14, the first set of fibrils of the tubular member are axially aligned with the plurality of struts.

According to another example, ("Example 16") further to Examples 11-14, the tubular member forms a continuous flow lumen.

According to another example, ("Example 17"), a method includes deploying an implantable medical device into a body, the implantable medical device including a frame having a plurality of struts overlapping and extending between a proximal end and a distal end of the frame and a tubular member attached to the frame having fibrils extending along the plurality of struts in alignment with the plurality of struts; and maintaining alignment of the fibrils with the plurality of struts in response to altering a geometry of the stent.

According to another example, ("Example 18") further to Example 17, maintaining alignment of the fibrils includes the fibrils shearing relative to one another to maintain alignment with the plurality of struts in response to at least one of a length change of the frame and a circumferential change of the frame.

According to another example, ("Example 19") further to Examples 17 or 18, the fibrils of the tubular member are axially aligned with the plurality of struts.

According to another example, ("Example 20") further to Examples 17-19, the plurality of struts are braided and extend helically between the proximal end and the distal end of the frame, and the fibrils are configured to coincide with a geometry of the plurality of struts.

According to another example, ("Example 21"), an implantable medical device includes a frame having at least one strut arranged in a first direction; and a tubular member attached to the frame and including a strength element oriented with the at least one strut in the first direction and the strength element is configured to bias the at least one strut in the first direction.

BRIEF DESCRIPTION OF THE DRAWINGS

FIG. 7A shows an image of an example tubular member having a strength aligned in a first direction, consistent with various aspects of the present disclosure.

FIG. 7B shows a close-up view of the image of an example tubular member, in FIG. 7B, consistent with various aspects of the present disclosure.

DETAILED DESCRIPTION

Persons skilled in the art will readily appreciate that various aspects of the present disclosure can be realized by any number of methods and apparatuses configured to perform the intended functions. It should also be noted that the accompanying figures referred to herein are not necessarily drawn to scale, but may be exaggerated to illustrate various aspects of the present disclosure, and in that regard, the figures should not be construed as limiting.

A medical device, consistent with various aspects of the present disclosure, is a device adapted to be inserted into a body and then deployed within the body. Such medical devices may be deployed within an artery or other vessel. Most generally, medical devices according to various examples assist in structurally supporting the host vessel lumen, maintaining patency through the vessel, passageway or opening, repairing vessels having an intimal flap or dissection, or isolating sections of a host vessel lumen, such as aneurysms. The medical devices may be shaped and sized and otherwise customized to fit a particular anatomy, including adjusting its length and inside diameters. The medical devices may include a stent with a framework of struts (or relatively rigid sections) and also may include a graft coupled or attached to the framework of struts.

Grafts or coverings in combination with the stent may help minimize or at least reduce the risk of introduction of emboli into a bloodstream, resist tissue encroachment into the lumen defined by the stent, reduce pressure on a weakened part of a blood vessel to reduce the risk of vessel rupture, and/or to create a conduit for attaching at least two vessels. The grafts or coverings may be made from continuous materials with no holes visible without magnification. Various grafts or coverings may be attached to the luminal (interior) or exterior surface of the stent.

In addition, the medical devices discussed herein may include braided or helical frames. The braided or helical frames may include a plurality of struts that overlap as the plurality of struts extends between ends of the medical devices. During deployment, geometry change, or other shape change of the braided frames, helical frames, or other frames, a graft or covering attached to the stent may encumber the stent's ability to expand. As discussed in further detail below, the medical devices discussed herein include tubular members (e.g., grafts or coverings) that interact and cooperate with the framework (to which the tubular members are attached) to ensure accurate deployment and functioning of the medical devices, for example with an inelastic or substantially inelastic covering or tube.

Figure 1:
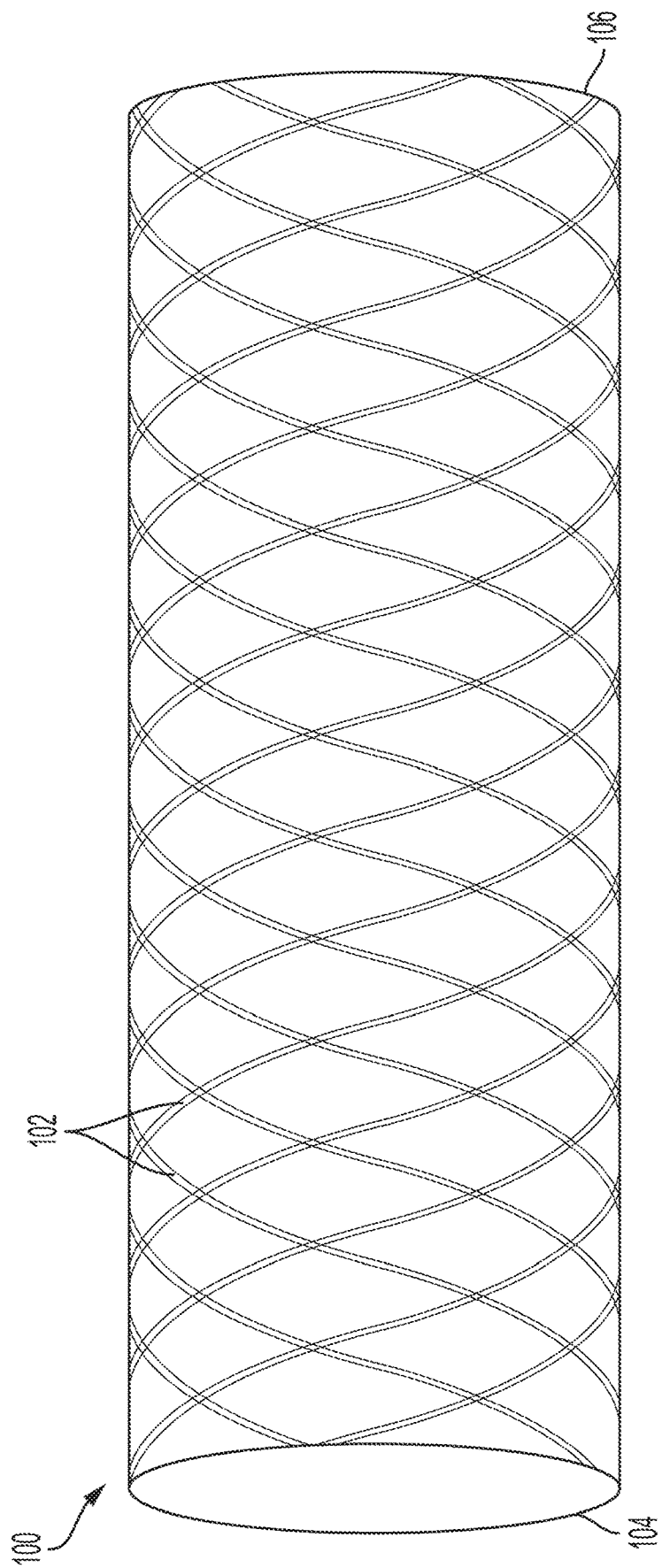
FIG. 1 shows an example stent, consistent with various aspects of the present disclosure.
Figure 2:
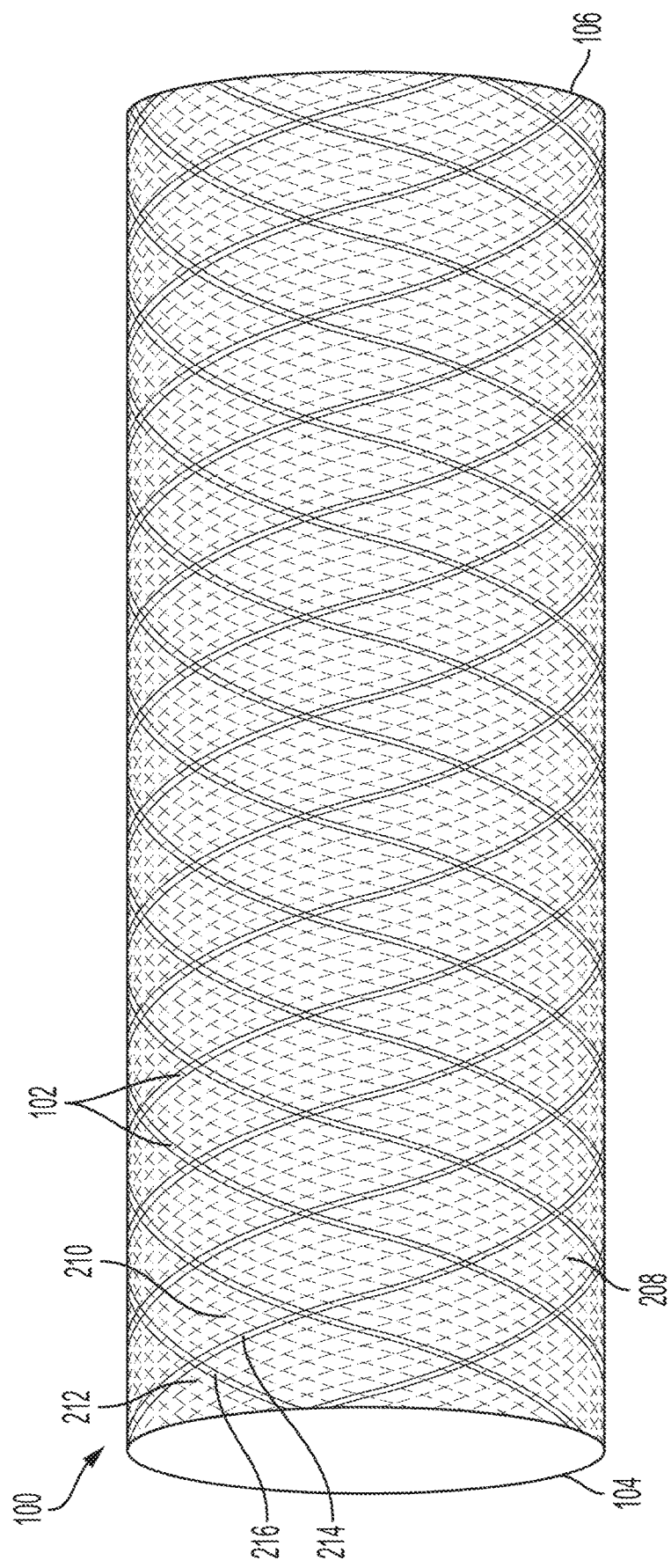
FIG. 2 shows an example stent and tubular member in a non-deformed configuration, consistent with various aspects of the present disclosure.
Figure 5:
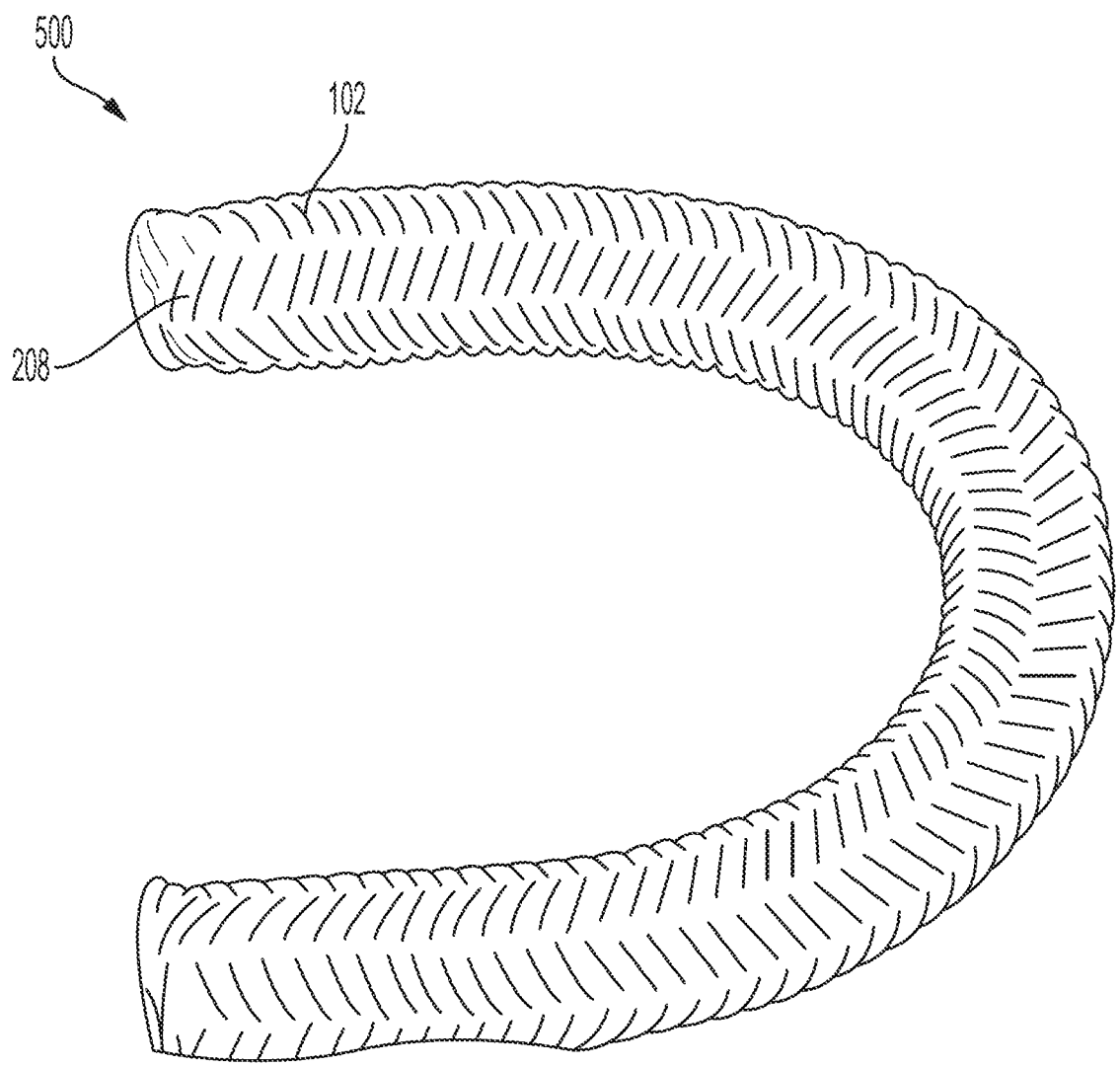
FIG. 5 shows another example stent and tubular member, consistent with various aspects of the present disclosure.

FIG. 1 shows an example stent 100, consistent with various aspects of the present disclosure. The stent 100 (or frame) includes a plurality of struts 102 that extend between a proximal end 104 and a distal end 106 of the stent 100. The stent 100 may be a support structure for an implantable medical device (e.g., an occluder, filter, or other similar device) formed by the plurality of struts 102. As shown in FIG. 1, the struts 102 form a tubular structure and it is understood that the struts 102 may form a non-cylindrical structure in certain instances. The plurality of struts 102 may overlap between the proximal end 104 and the distal end 106 of the stent 100. The plurality of struts 102 may be considered a braided stent. In addition, the plurality of struts 102 traverse a circumference of the stent 100 in lengthwise but angularly intersecting directions. The two directional sets of struts are interlaced or interwoven to form a tubular, supportive structure. In certain instances, the stent 100 may be a helical construct FIG. 2 shows an example stent 100 and tubular member 208 in a non-deformed configuration, consistent with various aspects of the present disclosure. The stent 100 and tubular member 208 form an implantable medical device. The tubular member 208 may be formed of an oriented polymer with a low shear strength direction (e.g., expanded PTFE (ePTFE)). The tubular member 208 may have a strength in one direction that is higher than a strength in another direction such that when a shear force is induced on or to the tubular member 208 (e.g., by way of stent 100 altering shape), the tubular member 208 is configured to reorient with the shear force. The tubular member 208 may stretch without wrinkling or tearing. The tubular member 208 is configured to move in tandem with the stent 100. In this regard, the tubular member 208 may include fibrils 210, 212, which are labeled and are represented generally in FIG. 2. It should be understood that, according to various embodiments, the fibrils 210, 212 are not readily seen by the naked eye (e.g., as shown in FIG. 5). As shown, the tubular member 208 may include fibrils 210, 212 that are aligned with the plurality of struts 102. The fibrils 210, 212 optionally extend along the plurality of struts 102 and are aligned with the plurality of struts 102, according to various embodiments.

As shown in FIG. 2, the plurality of struts 102 form a frame by overlapping and helically extending between the proximal end 104 and the distal end 106 of the medical device. The plurality of struts 102 are wound such that adjacent ones of the plurality of struts 102 extend in opposite directions (e.g., left handed and right handed helices). For example, a first strut 214 of the plurality of struts 102 may extend upward and toward the proximal end 104 at a location on the stent 100, whereas the second strut 216

(adjacent to the first strut 214) of the plurality of struts 102 extends upward and toward the distal end 106 of the stent 100 at that particular location. The first strut 214 represents a left handed helix, and the second strut 216 represents a right handed helix. Although the stent 100 includes a plurality of struts 102, single ones of the first strut 214 and the second strut 216 are highlighted for ease of understanding. Various other struts are shown in FIG. 2 and are arranged and extend similarly to the designated first strut 214 and designated second strut 216, and as such are similarly considered to be a first strut 214 and second strut 216.

In certain instances, the fibrils 210, 212 of the tubular member 208 are axially aligned with the plurality of struts 102. For example, tubular member may include a first set of fibrils 210 and a second set of fibrils 212 as shown in FIG. 2. The first set of fibrils 210 may be aligned with the helices of the first direction (e.g., the second strut 216 of the plurality of struts 102) and the second set of fibrils 212 may be aligned with the helices of the second direction (e.g., the first strut 214 of the plurality of struts 102). In certain instances, the fibrils 210, 212 extend in parallel with the plurality of struts 102. For example, the first set of fibrils 210 extend parallel to the first struts 214 and other similarly extending struts of the plurality of struts 102 shown in FIG. 2 and the second set of fibrils 212 and other similarly extending struts of the plurality of struts 102 shown in FIG. 2. Although the tubular member 208 includes multitude of fibrils 210, 212, single ones of the first set of fibrils 210 and the second set of fibrils 212 are highlighted for ease of understanding. The other fibrils shown in FIG. 2 that are arranged and extend similarly to the designated one of the first set of fibrils 210 and designated one of the second set of fibrils 212 are also considered to be, respectively, part of the first set of fibrils 210 and the second set of fibrils 212.

In certain instances, the plurality of struts 102 are braided and extend helically between the proximal end 104 and the distal end 106. The fibrils 210, 212 are configured to align with a geometry of the plurality of struts 102. For example, the fibrils 210, 212 extend at the same pitch angle at which the plurality of struts 102 extend. In addition and as noted above, the plurality of struts 102 are angled such that adjacent ones of the plurality of struts 102 extend in intersecting directions to form the braided stent 100. The first strut 214 and the first set of fibrils 212 may extend upward and toward the proximal end 104 at a location on the stent 100, whereas the second strut 216 (adjacent to the first strut 214) and the second set of fibrils 212 extends upward and toward the distal end 106 of the stent 100 at that particular location.

In addition to being aligned with the plurality of struts 102, the fibrils 210, 212 are configured to maintain alignment with the plurality of struts 102. The fibrils, for example, maintain alignment with the plurality of struts 102 when the stent 100 changes configuration, geometry, or shape as is described in further detail with reference to FIG. 3.

Figure 3:
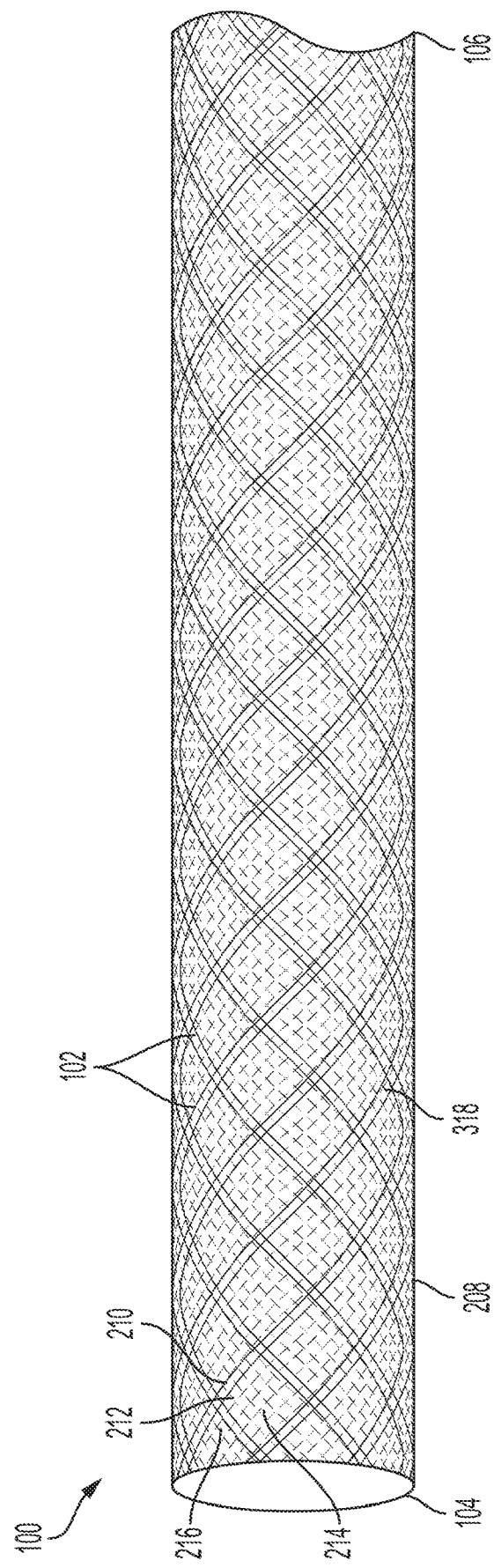
FIG. 3 shows another example stent and tubular member in a deformed configuration, consistent with various aspects of the present disclosure.

FIG. 3 shows another example stent 100 and tubular member 208 in a deformed configuration, consistent with various aspects of the present disclosure. As compared to the stent 100 and tubular member 208 shown in FIG. 2, the stent 100 and tubular member 208 have been reduced in circumference (e.g., compressed) and elongated. The deformed configuration shown in FIG. 3, may be a delivery configuration for the stent 100 and tubular member 208, or a configuration of the stent 100 and tubular member 208 as the result of forces acting on the stent 100 and/or the tubular member 208 (e.g., after implantation in a patient).

As noted above with reference to FIG. 2, for example, fibrils 210, 212 are configured to maintain alignment with the plurality of struts 102 in addition to being aligned with the plurality of struts 102. The fibrils, for example, maintain alignment with the plurality of struts 102 when the stent 100 changes configuration, geometry, or shape. As shown in FIG. 3, the plurality of struts 102 have reoriented as a result of being reduced in diameter. Due to the helical/braided configuration of the plurality of struts 102, the stent 100 has also elongated in comparison to the non-deformed or non-altered stent 100 shown in FIG. 2. The angle at which the plurality of struts 102 extend helically has also decreased relative to the non-deformed or non-altered stent 100 shown in FIG. 2. For example, in some examples the angle by which the plurality of struts 102 extend helically changes by greater than zero and less than 90 degrees according to various examples when the stent is transitioned from the first to the deformed state. The fibrils 210, 212 also change pitch angle in the same manner in which the plurality of struts 102 change pitch angle as shown in FIG. 2. The stent 100 and the tubular member 208 deform in conjunction with one another by way of the plurality of struts 102 and the fibrils 210, 212 re-orienting in tandem.

In certain instances, a geometry of the plurality of struts 102 changes in response to at least one of a length change of the stent 100 (e.g., the frame), a circumferential change of the stent 100, or angular displacement of the struts of the stent 100. Similarly, the fibrils 210, 212 are configured to orient with the plurality of struts 102. The fibrils 210, 212 and the plurality of struts 102 orient in a direction extending toward the proximal end 104 of the stent 100 and a direction extending toward the distal end 106 of the stent 100. In certain instances, the plurality of struts 102 include a first set of struts, represented by the first strut 214, that extend at a first pitch toward the proximal end 104 and a second set of struts, represented by the second strut 216, that extend at a second pitch toward the distal end 106. Similarly, the first set of fibrils 210 extend at approximately the first pitch toward the proximal end 104 and the second set of fibrils 212 extend at approximately the second pitch toward the distal end 106. As shown in comparing FIG. 2 and FIG. 3, the first set of fibrils 210 and the first set of struts, represented by the first strut 214, alter pitch angles in coordination with one another, and the second set of fibrils 212 and the second set of struts, represented by the second strut 216, alter pitch angles in coordination with one another.

In certain instances, the first set of fibrils 210 overlap with the second set of fibrils 212 throughout the tubular member 208. In response to at least one of a length change of the stent 100, a circumferential change of the stent 100 (e.g., as shown comparing FIG. 2 and FIG. 3) or angular displacement of the struts of stent 100, the fibrils 210, 212 are configured to shear (or slip) relative to one another to maintain alignment of the fibrils 210, 212 with the plurality of struts 102. The fibrils 210, 212, for example, shear within the tubular member 208 to maintain alignment with the plurality of struts 102. The tubular member 208 forms a continuous flow lumen by way of the fibrils 210, 212. The tubular member 208 may be an impermeable membrane or film.

In certain instances, the fibrils 210, 212 being configured to maintain orientation with the plurality of struts 102 allows the stent 100 to expand and contract in response to at least one of a length change of the frame, a circumferential change of the stent 100, or angular displacement of the struts of the stent 100. The fibrils 210, 212 do not otherwise encumber or restrict the ability of the stent 100 to change geometry or expand and contract. More specifically and in certain instances, the tubular member 208, by way of the fibrils 210, 212, is configured to resist residual elastic strain acting against stent 100 deformation in response to at least one of the length change of the frame, the circumferential change of the stent 100, or angular displacement of the struts of the stent. The tubular member 208 does not include residual elastic strain that acts against the stent 100 changing geometry under deformation of the stent 100.

The tubular member 208 may include non-oriented fibrils 318 in addition to the fibrils 210, 212 that are not oriented with the plurality of struts 102. The non-oriented fibrils 318 (represented by the open space between the fibrils 210, 212) may fill connect and fill space between the fibrils 210, 212. The non-oriented fibrils 318 are those fibrils of the tubular member 208 that are not oriented or aligned with primary strength of the tubular member 208.

The fibrils 210, 212 that are aligned with struts 102 of the stent 100 may have a greater strength than fibrils or nodes that connect the strength fibrils together For example, the tubular member can be made from a film that has a force to break strength direction of 1.06 kgf/cm and a force to break transverse direction strength of 0.024 kgf/cm as measured by a tensile testing machine. Other ratios of strength to transverse direction may be used dependent on application. For example a ratio of strength direction to transverse direction may be 30, 35, 40, 45, 50, 55, 60 or more. In addition, the fibrils 210, 212 that are aligned with struts 102 of the stent 100 also have a greater length greater than lengths of the fibrils that are unaligned with the struts 102 of the stent 100 and also maintain alignment with the struts 102 of the stent 100.

In certain instances, the tubular member 208 may include a single set of fibrils 210 that are aligned with struts 102 of the stent 100. The tubular member 208 may have a single strength direction oriented with the stent 100.

Figure 4A:
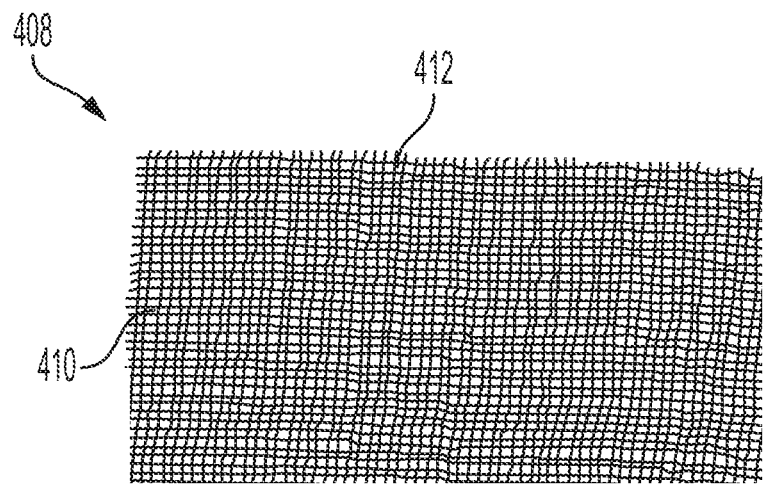
FIG. 4A shows another example tubular member in an undeformed state, consistent with various aspects of the present disclosure.
Figure 6:
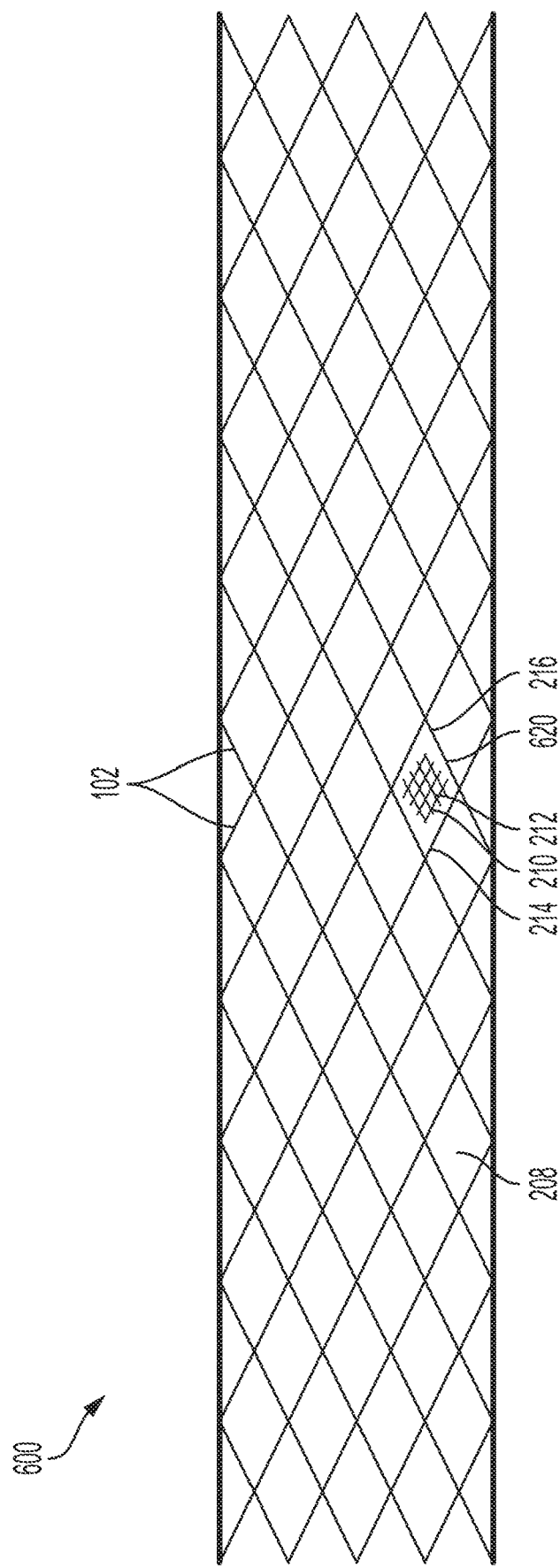
FIG. 6 shows an example laser-cut stent, consistent with various aspects of the present disclosure.

FIG. 4A shows another example tubular member 408 in an undeformed state, consistent with various aspects of the present disclosure. The tubular member 408 is a weave or knit material. The tubular member 408 may have a strength element that is aligned with one or more struts of a stent (e.g., as shown in FIG. 1 or FIG. 6). The tubular member 408 may be attached to a stent that is a continuous frame, as depicted in FIG. 1 or FIG. 6 or a plurality of discrete rings to form a stent frame. In addition, the tubular member r408 may be configured to maintain orientation of the strength element with the strut on response to a force applied to the stent. The strength element of the tubular member 408 is configured to maintain orientation in response to a force acting on the tubular member 408.

As shown in FIG. 4A, the tubular member 408 member includes a series or woven or knit filaments, threads, or fibers 410, 412. The filaments, threads, or fibers 410, 412 may form the strength element. In addition, the tubular member 408 may have a strength in one direction that is higher than a strength in another direction such that when a shear force is induced on or to the tubular member 408 (e.g., by way of stent 100, to which the tubular member 408 is attached, altering shape), the tubular member 408 is configured to reorient with the shear force as shown in FIG. 4B.

Figure 4B:
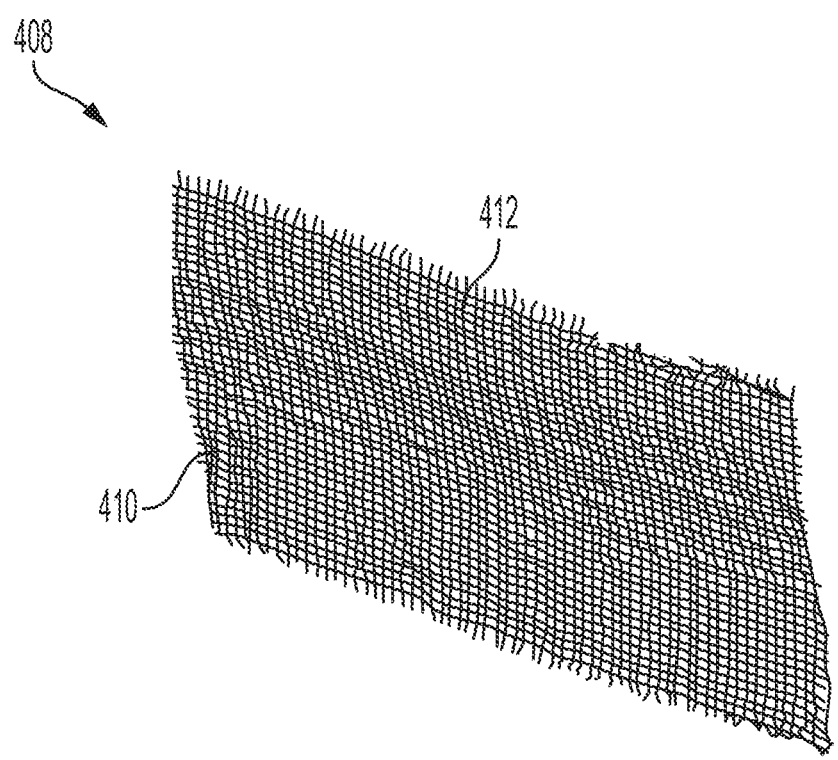
FIG. 4B shows another example tubular member in a deformed state, consistent with various aspects of the present disclosure.

As shown in FIG. 4B, the tubular member 408 may stretch without wrinkling or tearing. The tubular member 408 is configured to move in tandem with the stent 100. The tubular member 408 is oriented along with a stent 100, to which the tubular member 408 is coupled to or attached to, maintain orientation of the strength element with the at least one strut in response to a force applied to the frame.

FIG. 5 shows another example stent 100 and tubular member 208, consistent with various aspects of the present disclosure. In certain instances, the tubular member 208 is coupled to the stent 100, having a plurality of struts 102, to form a medical device 500. In certain instances, the tubular member 208 may be formed of expanded PTFE (ePTFE) and attached to the stent 100 using fluorinated ethylene propylene (FEP). The tubular member 208 may be arranged on one side or both sides of the stent 100. The tubular member 208 is attached to the stent 100, in certain instances, such that fibrils contained in the tubular member 208 are aligned with struts that form the stent 100.

The illustrative medical device shown in FIG. 5 is not intended to suggest any limitation as to the scope of use or functionality of embodiments as discussed throughout this disclosure. Neither should the illustrative system be interpreted as having any dependency or requirement related to any single component or combination of components illustrated therein. For example, in various embodiments, the illustrative medical device 500 may have fibrils that are continued to maintain orientation with a plurality of struts of the stent 100 as described with reference to FIG. 1-3. In addition, the tubular member 208 may include a primary strength oriented with the plurality of struts as discussed with reference to FIG. 4.

FIG. 6 shows an example laser-cut stent 600, consistent with various aspects of the present disclosure. The stent 600 may include a plurality of diamond shaped cells 620 (one of which is highlighted in FIG. 6), although the cells 620 may have different shapes such as chevron or rectangle. The laser-cut stent could be a continuous frame as depicted or a plurality of discrete rings to form a stent frame. In addition, the laser-cut stent 600 may include a tubular member 208 attached thereto. As discussed in further detail above, the tubular member 208 may be formed of a polymer with a low shear strength direction (e.g., expanded PTFE (ePTFE)). The tubular member 208 may have a strength in one direction that is higher than a strength in another direction such that when a shear force is induced on or to the tubular member 208 (e.g., by way of stent 600 altering shape), the tubular member 208 is configured to reorient with the shear force. The tubular member 208 may stretch without wrinkling or tearing. The tubular member 208 is configured to move in tandem with the stent 600. In this regard, the tubular member 208 may include fibrils 210, 212, which are labeled and are represented generally in FIG. 6.

As shown in FIG. 6, the stent 600 includes overlapping or crossing struts 102. Although the stent 600 includes a plurality of struts 102, single ones of a first strut 214 and a second strut 216 are highlighted for ease of understanding. Various other struts are shown in FIG. 2 and are arranged and extend similarly to the designated first strut 214 and designated second strut 216, and as such are similarly considered to be a first strut 214 and second strut 216. The fibrils 210, 212 of the tubular member 208 are axially aligned with the plurality of struts 102. For example, tubular member may include a first set of fibrils 210 and a second set of fibrils 212 as shown in FIG. 2. The first set of fibrils 210 may be aligned with the first strut 214 of the plurality of struts 102, and the second set of fibrils 212 may be aligned with the second strut 216 of the plurality of struts 102. In certain instances, the fibrils 210, 212 extend in parallel with the plurality of struts 102. Although the tubular member 208 includes multitude of fibrils 210, 212, single ones of the first set of fibrils 210 and the second set of fibrils 212 are highlighted for ease of understanding. The other fibrils of the tubular member 208 that are arranged and extend similarly to the designated one of the first set of fibrils 210 and designated one of the second set of fibrils 212 are also considered to be, respectively, part of the first set of fibrils 210 and the second set of fibrils 212.

In addition to being aligned with the plurality of struts 102, the fibrils 210, 212 are configured to maintain alignment with the plurality of struts 102. The fibrils, for example, maintain alignment with the plurality of struts 102 when the stent 100 changes configuration, geometry, or shape.

FIG. 7A shows an image of an example tubular member 208 having a strength aligned in a first direction 722, consistent with various aspects of the present disclosure. The strength may be associated with fibrils 212 within the tubular member 208. In addition, the strength of the tubular member 208 may be aligned with a strut of a stent to which the tubular member 208 is attached as discussed in detail above. The tubular member 208 being attached to a stent and aligns the strength of the tubular member 208 with a strut in the first direction 722. As a result, the tubular member 208 is configured to bias the strut in the first direction 722.

FIG. 7B shows a close-up view of the image of an example tubular member 208, in FIG. 7B, consistent with various aspects of the present disclosure.

Suitable materials for use in in the tubular member 208 may include, without limitation, fluoropolymers (especially polytetrafluoroethylene (PTFE) and fluorinated ethylene propylene (FEP)), polyethylenes, polyethylene terephthalate (PET), nylon, polyurethane, polypropylene, polyester, polyimide, etc., as well as composite materials combining these and/or other materials to achieve the desired strength and compliance characteristics. Expanded PTFE (ePTFE) is believed to be most preferred for many applications.

Depending on applications, tubular members of the present disclosure may be constructed from a continuous material, such as continuous films, tapes, or sheets of materials. Alternatively, the tubular members may include discontinuous structures, such as sheets or tapes that include holes or slits therein, or even materials formed from weaves, knits, or other open structures.

Consistent with various aspects of the present disclosure, frames discussed herein may be made from a variety of materials. These materials comprise metals, such as nitinol, stainless steel, tantalum, titanium, tungsten, gold, platinum, iridium, rhodium and alloys thereof or pyrolytic carbon. Other materials comprise polymers such as polyurethane, high density polyethylene, polypropylene, and poly(dimethyl siloxane). Further still, the frames may be formed from biocompatible polymers that are bio-resorbable (e.g., bio-erodible or bio-degradable). Bio-resorbable materials are preferably selected from the group consisting of any hydrolytically degradable and/or enzymatically degradable biomaterial. Examples of suitable degradable polymers include, but are not limited to, polyhydroxybutyrate/polyhydroxyvalerate copolymers (PHV/PHB), polyesteramides, polylactic acid, hydroxy acids (i.e. lactide, glycolide, hydroxybutyrate), polyglycolic acid, lactone based polymers, polycaprolactone, poly(propylene fumarate-co-ethylene glycol) copolymer (aka fumarate anhydrides), polyamides, polyanhydride esters, polyanhydrides, polylactic acid/polyglycolic acid with a calcium phosphate glass, polyorthesters, silk-elastin polymers, polyphosphazenes, copolymers of polylactic acid and polyglycolic acid and polycaprolactone, aliphatic polyurethanes, polyhydroxy acids, polyether esters, polyesters, polydepsidpetides, polysaccharides, polyhydroxyalkanoates, and copolymers thereof. Further still, the tubes may be formed of a polycarbonate material, such as, for example, tyrosine-derived polycarbonates, tyrosine-derived polyarylates, iodinated and/or brominated tyrosine-derived polycarbonates, iodinated brominated tyrosine-derived polyarylates polyhydroxy acids, polyorthoesters, polyether esters, polyesters, polyamides, polyesteramides, polydepsidpetides, aliphatic polyurethanes, polysaccharides, polyhydroxyalkanoates, and copolymers thereof.

Additionally, the frames could be comprised of any number of other polymers. In another embodiment, metals and polymers may be used to fabricate said tube in a composite, laminate reinforced material, or one that is simply coated with the material. Depending on desired characteristics, tubes may be constructed of materials with specific attributes. For example, in applications where the tube will be expanded and must remain so with little or no creep or re-constriction (that is it must "lock in place"), plastically deformable materials may be chosen for monolithic constructs. Conversely, should a tube need to remain compliant, meaning remaining capable of some degree of radial re-contraction and re-expansion, elastic materials may be chosen. It will be recognized that combining materials with different functional or behavioral attributes may be effected in selected instances. The configuration of the tubes of the invention may be varied to produce selected benefits. In one embodiment, the components making up the frames (the struts) are asymmetrically wrapped along the entire length of the frame. However, in other embodiments, asymmetrically-wrapped frames can be interspersed and connected to torsionally-stable symmetrically-wrapped tube sections, the latter serving to transmit torque.

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting.

What is claimed is:

1. An implantable medical device comprising:
   a frame having a plurality of struts overlapping and extending between a proximal end and a distal end of the frame; and
   a continuous film formed of expanded polytetrafluoroethylene (ePTFE) defining a tubular member attached to the frame, the continuous film having a microstructure of nodes and fibrils, the continuous film being oriented with the frame such that the fibrils extend along and are axially aligned with the plurality of struts, the fibrils configured to shear relative to one another within the continuous film to facilitate maintaining alignment with the plurality of struts in response to at least one of a length change of the frame and a circumferential change of the frame, wherein the plurality of struts are braided and extend helically between the proximal end and the distal end of the frame, and the fibrils are configured to coincide with a geometry of the plurality of struts.

2. The implantable medical device of claim 1, wherein the fibrils extend in parallel with the plurality of struts.

3. The implantable medical device of claim 1, wherein the geometry of the plurality of struts changes in response to at least one of the length change of the frame and the circumferential change of the frame, and the fibrils are configured to orient with the plurality of struts in a direction extending toward the proximal end of the frame and a direction extending toward the distal end of the frame.

4. The implantable medical device of claim 1, wherein the plurality of struts include a first set of struts that extend at a first pitch toward the proximal end and a second set of struts that extend at a second pitch toward the distal end, and the fibrils include a first set of fibrils that extend at approximately the first pitch toward the proximal end and a second set of fibrils that extend at approximately the second pitch toward the distal end.

5. The implantable medical device of claim 4, wherein the first set of fibrils overlap with the second set of fibrils throughout the tubular member.

6. The implantable medical device of claim 1, wherein the tubular member is configured to allow expansion and contraction of the frame in response to at least one of the length change of the frame, the circumferential change of the frame, and an angular displacement of the frame.

7. The implantable medical device of claim 6, wherein the tubular member is configured to resist residual elastic strain acting against frame deformation in response to at least one of the length change of the frame, the circumferential change of the frame, and the angular displacement of the frame.

8. A method comprising:
   deploying an implantable medical device into a body, the implantable medical device including a frame having a plurality of struts overlapping and extending between a proximal end and a distal end of the frame and a continuous film formed of expanded polytetrafluoroethylene (ePTFE) and defining a tubular member attached to the frame, the continuous film having a microstructure of nodes and fibrils, the continuous film being oriented with the frame such that the fibrils extend along and are axially aligned with the plurality of struts in alignment with the plurality of struts; and
   maintaining alignment of the fibrils by shearing relative to one another to maintain alignment with the plurality of struts in response to at least one of a length change of the frame and a circumferential change of the frame with the plurality of struts in response to altering a geometry of the stent, wherein the plurality of struts are braided and extend helically between the proximal end and the distal end of the frame, and the fibrils are configured to coincide with a geometry of the plurality of struts.

9. The method of claim 8, wherein maintaining alignment of the fibrils includes the fibrils shearing relative to one another to maintain alignment with the plurality of struts in response to at least one of the length change of the frame and the circumferential change of the frame.

10. An implantable medical device comprising:
   a frame having a plurality of struts overlapping and extending between a proximal end and a distal end of the frame; and
   a continuous film formed of expanded polytetrafluoroethylene (ePTFE) defining a tubular member attached to the frame, the continuous film having a microstructure of nodes and fibrils, the continuous film being oriented with the frame such that the fibrils extend along and are axially aligned with the plurality of struts, the fibrils configured to shear relative to one another within the continuous film to facilitate maintaining alignment with the plurality of struts in response to at least one of a length change of the frame and a circumferential change of the frame, wherein the plurality of struts include a first set of struts that extend at a first pitch toward the proximal end and a second set of struts that extend at a second pitch toward the distal end, and the fibrils include a first set of fibrils that extend at approximately the first pitch toward the proximal end and a second set of fibrils that extend at approximately the second pitch toward the distal end.

* * * * *